United States Patent [19]

Buerger

[11] 3,979,264

[45] Sept. 7, 1976

[54] BAND FOR CARRYING OUT MICROBIOLOGICAL EXAMINATIONS

[76] Inventor: Heinz Buerger, Kaiserstrasse 25, 6500 Mainz, Rhineland 1, Germany

[22] Filed: Mar. 31, 1975

[21] Appl. No.: 563,839

[52] U.S. Cl. .......................... 195/139; 195/103.5 R
[51] Int. Cl.² ......................................... C12K 1/10
[58] Field of Search ...................... 195/103.5 R, 139

[56] References Cited
UNITED STATES PATENTS

| | | | |
|---|---|---|---|
| 3,128,239 | 4/1964 | Page ................................. | 195/139 |
| 3,129,144 | 4/1964 | Page et al. .......................... | 195/139 |

*Primary Examiner*—A. Louis Monacell
*Assistant Examiner*—Robert J. Warden
*Attorney, Agent, or Firm*—Woodhams, Blanchard and Flynn

[57] ABSTRACT

A device for carrying out microbiological examinations. There is provided a base for carrying a large number of samples of bacteria supporting nutrient material comprising an elongated strip of flexible material such as a material similar to photographic film. The bacteria supporting nutrient is applied at selected intervals in one or more bands along the length of the material. Spacers are provided on the material to enable same to be rolled or folded without disturbing the bacteria supporting nutrients. Irregularities, such as perforated knobs are provided along the length of said material for the anchoring thereon of said nutrient material. The elongated material may be rolled or folded for storage and/or incubation as desired, and subsequently unrolled for examination. The device may also be used for testing a resistance of bacteria to bacteriacides.

18 Claims, 3 Drawing Figures

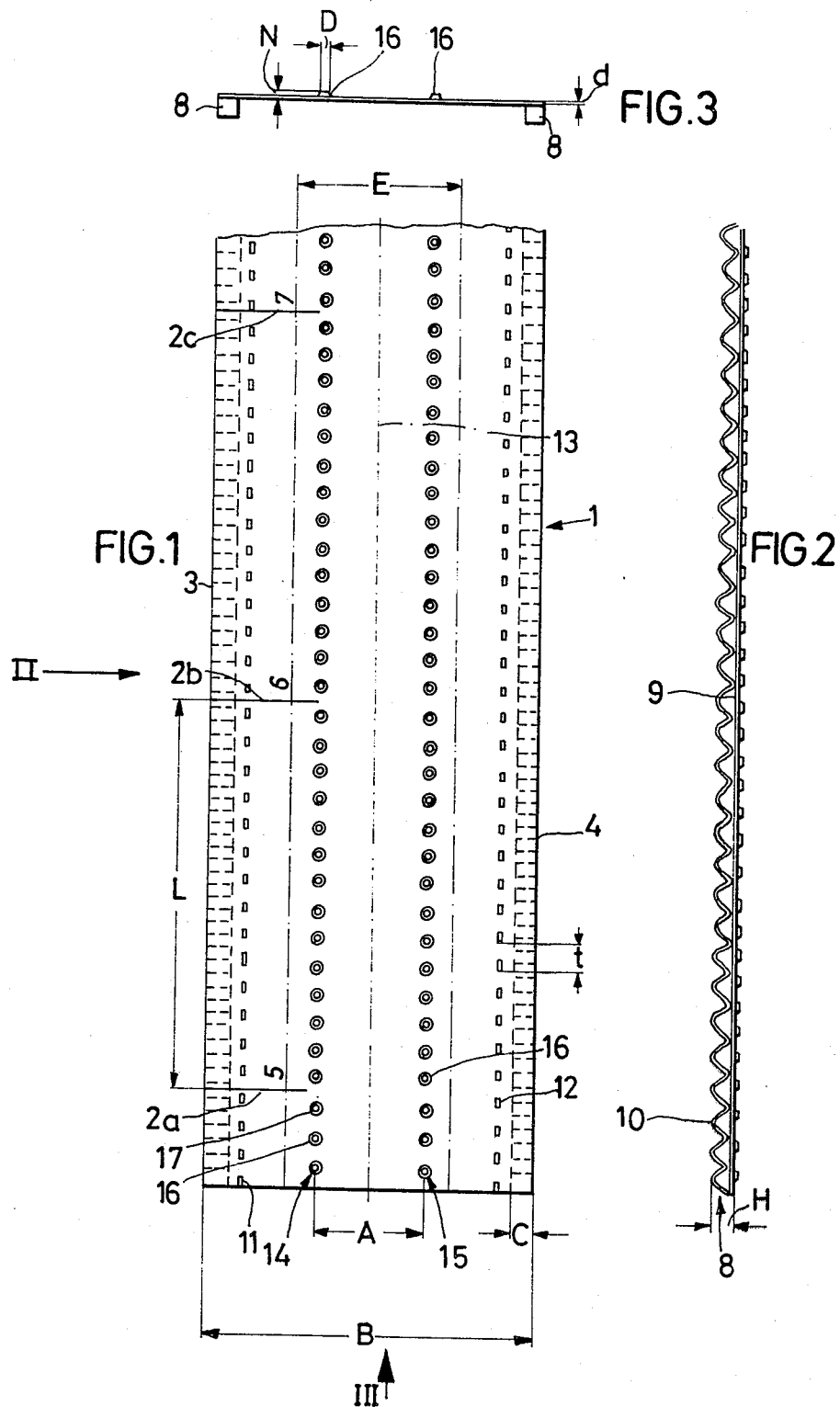

BAND FOR CARRYING OUT MICROBIOLOGICAL EXAMINATIONS

FIELD OF THE INVENTION

The differentiating of microorganisms assumes usually their isolation in form of individual colonies on a semisolid nutrient media. In order to obtain the desired individual colonies, there is usually produced on the surface of the semisolid nutrient medium a dilute smear (or dilute inoculation) by means of a smear needle or smear loop. The bacteria which are attached to the smear instrument are transferred to the surface of the semisolid medium and are distributed in a thin layer. By controlling the length of the smear, the number of transmitted bacteria is reduced until finally only individual microorganisms remain on the trace of the smear instrument. The purpose of the smear is to obtain colonies, which consist only of the progeny of one single microorganism which remained in the sliding trace (Clon). These colonies can then be further processed for differentiating the microorganisms.

BACKGROUND OF THE INVENTION

Carriers of the semisolid medium have for several decades usually been Petri dishes. These are adjusted in form and size to the manual operation. To carry out a series of examinations by means of Petri dishes requires a considerable work input and much space. The large amount of work results from having to individually and manually handle each individual dish. To create a smear by hand requires a certain skill on the part of the laboratory technician and requires for each smear, together with such side operations as inscribing on the Petri dish, taking the sample and annealing of the needles, approximately 1 minute of time. Also to introduce the nutrient medium into the dish is time-consuming because every dish must be handled separately. The large space requirement results primarily from having to store a large number of dishes in an incubation closet. Also the conventional process involves the danger of sample exchanges, because each individual Petri dish must be individually identified, which is difficult and is subject to error.

It is also known (German Offenlegungsschrift No. 2,055,741), to use nutrient medium carriers which are not entirely solid and which are intended for a one-time use only. In the use of such carriers, the work which is otherwise connected with cleaning the Petri dishes is eliminated but this procedure still involves a considerable work input. Also with respect to the space needed in incubation closets, such throw-away nutrient medium carriers present no step forward.

SUMMARY OF THE INVENTION

The principal object of the invention is to produce a band with which microbiological examinations can be carried out with less work input, less space requirement and less risk of error.

To attain this object a flexible band has been produced, which carries a semisolid or solid nutrient medium, which is adaptable to inoculation in microbiological examinations, which has sufficient length that several samples can be applied successively and which can be rolled or folded, whereby spacers extend along the band, which spacers keep adjacent parts of the band separated from one another.

By using such a band, series examinations can be carried out much more economically and swiftly, because the band-shaped carrier can be guided past an automatic smear device which assures an even quality of the smear independent of the degree of skill and accuracy of a laboratory technician. The danger of sample exchanges is considerably reduced, because the arrangement of a number of samples on the band-shaped carrier provides a nondestroyable order of the samples. A very important advantage is also the considerable volume reduction. For each sample, the inventive band requires only approximately one seventh of the space, which is required when Petri dishes are used. Also the nutrient medium requirement (nutrient media are relatively expensive) can be reduced considerably. Practical experiments have found that only approximately 40% of the present requirement is needed. The spacers act, without the application of special measures, to prevent the nutrient media from being touched, when the band is rolled or folded. Also due to the distance between the individual layers the gas exchange required for an unhindered multiplication of the bacteria is possible.

BRIEF DESCRIPTION OF THE DRAWING

A band according to the invention is illustrated in the drawing, in which:

FIG. 1 is a top view of the band,

FIG. 2 is a side view of the band in the direction of the arrow II of FIG. 1, and FIG. 3 is a front view of the band in the direction of the arrow III of FIG. 1.

DETAILED DESCRIPTION

The band which is as a whole identified with reference numeral 1 may consist of a glass-clear, transparent material, as for example a transparent plastic, for example of the same material from which photographic films are made. The band may have a width B of for example 60 mm. The thickness d of the band material may lie within the range of 0.15 to 0.20 mm.

Markings 2a, 2b, 2c, are arranged longitudinally of the band, which markings are shown at regular intervals. Each marking has an ordinal number, in the illustrated case, marking 2a has the number 5, the marking 2b the number 6 and the marking 2c the number 7. The markings can be spaced apart at a distance L of for example 70 mm.

Along the edges 3 and 4 of the band extend spacers. Said spacers are formed in the illustrated exemplary embodiment by corrugated narrow bands 8, which are secured on the underside 9 of the band or film, for example by means of gluing. The height H of the individual corrugations 10 may be for example 4 mm and the space between the corrugations define a plurality of passageways. An advantageous width C of the corrugated bands 8 is for example also 4 mm.

Perforation rows 11 and 12 extend along the bands 8. The spacing T within the perforation rows can correspond to the normal spacing of perforations in a photographic film.

On both sides of the longitudinal center of the band 1, which center is defined by the dash-dotted line 13, rows 14 and 15 of knobs 16 are arranged. Said knobs may be impressions in the band material. The distance A between the rows 14 and 15 may for example be 20 mm. The height N of the knobs 16 may be for example 0.5 mm and their diameter D, for example 1.5 mm.

Perforations 17 exist at the highest points of the knobs, at the edges of which perforations the nutrient medium which is to be applied onto the foil is anchored.

In using the described film to carry our microbiological tests, the procedure is approximately as follows:

From a series of samples which are to be examined, a portion, the volume of which is determined by the shape of the smear instrument, for example a loop, is automatically taken and is transferred onto the band-shaped carrier which is coated with a nutrient medium and is spread out sufficiently, for example by means of further smear loops, that during the course of the smear individual colonies are with certainty created. Prior to this, the carrier is coated with a strip having a thickness, depending on the need, of 1–3 mm. and having a width E of for example 30 mm. and which consists of any desired semisolid agar medium.

It is of no importance for the process, whether the layer which is provided for raising the microorganisms consists of the common media produced on an agar base or of other layers which may be newly developed, for example layers which store better, or whether these media are worked into the carrier directly.

By each smear, which can be produced for example by three coordinately operating smear instruments, a surface of the band which is determined by two markings 2a, 2b, 2c is inoculated. With the mentioned dimensions of the band, the inoculated surface is approximately 60 × 30 mm. This surface corresponds in order of magnitude with the smear which is common in a Petri dish. However, the surface can be varied both in length and in width, without affecting the success of the smear. It is important only that as many individual colonies as possible are created which are suited for the further processing.

The surface intended for a dilute smear is determined by two factors, namely (1) by the size of the smear instrument and (2) by the band transport speed (if the band is moved relative to the smear instrument) or the speed of a carriage carrying the smear instrument (if the smear instrument is moved relative to the band). A relatively simple device is obtained if the smear instrument carries out only a reciprocal movement, while the band is moved continuously under the smear instrument.

The band may be moved by means of gears, which engage the perforations 11,12 or also by means of transport claws. The distance between two successive smears can be determined by the band transport speed. The smears may for example be separated from one another by a noninoculated surface of 30 × 10 mm.

The band transport can be coordinated with the transport of a sample chain. Furthermore, coordination with a sampling device to take out samples is necessary. The smear instruments are sterilized prior to their being used again, as a rule by means of heat. This may be done by means of a gas flame, resistance heating or inductive heating.

The band which is continuously coated with the nutrient medium can be wound during operation from one spool to another. Generally after the smearing is finished it is rolled back onto the original spool, to permit an evaluation in the sequence of the smeared samples. The spacers 8 prevent contact of the nutrient medium layer with the underside of the carrier and, further, a distance is maintained between the layers to permit a gas exchange (for example oxygen, carbon dioxide, etc,) through the passageways.

The inoculated, rolled up band can be incubated under any desired physical-chemical growth conditions (temperature, oxygen pressure, carbon dioxide pressure, etc.).

After a sufficient incubation time, the smears are evaluated. For this the band is rolled in a suitable device, which can consist substantially of two movable spools and a band guide, from one spool step-by-step to another spool, whereby the colony growth is judged and the individual colonies intended for differentiating are handled for further processing.

If in contrast to the described process, the band is used for determining the resistance of the bacteria, the number of colonies is determined and recorded as in the presently common operation. In order to prevent a migration of the bacteria, a control medium is added to the nutrient medium, such as a p-nitrophenylglycerin substance. A selected surface area is then evenly coated with a special inoculating device with the sample which is to be examined and subsequently small sheets soaked for example with antibiotics are placed onto the surface.

After the evaluation the band can be destroyed (for example by steam sterilization or by burning).

The band is coated with a nutrient medium which comprises an agar base by means of a coating device. The just barely liquid medium is then applied to the band under the usual sterile conditions. The applied layer is prevented from sliding off the foil by the knobs 16 with perforation 17 or by other irregularities with one or more perforations. Prior to its use the band must be stored corresponding with the requirements of the nutrient medium manufacturers.

The process is particularly suited when mass examinations must be carried out, as for example examinations which must be carried out within the scope of the disease or epidemiological laws. It is furthermore especially suited, when there is a special danger of infection during the processing of the test material and further, when, as is often the case in the first phase during processing of examination material, nausea-creating and badly smelling materials (stool, sputum, etc.) must be processed.

The embodiments of the invention in which an exclusive property or privilege is claimed are defined as follows:

1. In an elongated flexible band having a nutrient medium on a nutrient surface thereof intended for inoculation in microbiological examinations and further having a sufficient length for several samples to be applied in sequence, the improvement comprising a pair of spaced rows of longitudinal spacer means mounted on the opposite surface of said band, said spacer means being of a sufficient height above said opposite surface of said band to prevent the opposite surface of said band from contacting said nutrient surface and said nutrient medium thereon when said band is rolled or folded to effect an engagement of said nutrient surface with said spacer means, said spacer means defining passageway means extending laterally of said band to facilitate the lateral movement of a gas across said nutrient medium when said band is in a rolled or folded condition wherein the nutrient surface is engaging said spacer means.

2. The improvement according to claim 1, wherein said spacer means comprises two rows of narrow corrugated strips which are attached to said band.

3. The improvement according to claim 2, including a plurality of knobs on said band which serve to effect a holding of said nutrient medium on said band.

4. The improvement according to claim 2, wherein said passageway means is defined by the corrugations in said corrugated strips.

5. The improvement according to claim 4, wherein said spacer means have a height (H) of approximately 4 mm.

6. The improvement according to claim 1, wherein parallel to the longitudinal edges of said band there extends at least two rows of perforations which are arranged symmetrical to the longitudinal center of said band.

7. The improvement according to claim 1, wherein said spacer means comprise a plurality of longitudinally spaced members each having said sufficient height above said opposite surface.

8. The improvement according to claim 7, wherein said band has a plurality of knobs with perforations therethrough for effecting an anchoring of said nutrient medium to said band.

9. The improvement according to claim 8, wherein said perforations are arranged at the highest points of said spaced knobs.

10. The improvement according to claim 9, wherein said knobs have a height (N) of approximately 0.5 mm. and are arranged along two parallel rows which extend on both sides of the longitudinal center of said band and parallel to the longitudinal edges thereof.

11. The improvement according to claim 1, wherein said band is coated with a strip of sterile fabric to receive said nutrient medium thereon.

12. The improvement according to claim 1, including a plurality of markings to along the length of said band to define band sections.

13. The improvement according to claim 12, including numbering indicia adjacent said markings.

14. The improvement according to claim 1, wherein said band has a width (B) of approximately 60 mm. and is coated to a width (E) of approximately 30 mm. with said nutrient medium.

15. The improvement according to claim 1, wherein said nutrient medium has a thickness of between 1 mm. and 3 mm.

16. The improvement according to claim 1, wherein said nutrient medium is applied on both sides of said band.

17. The improvement according to claim 1, wherein said band consists of a plastic transparent foil.

18. A method for coating and inoculating a band comprising the steps of continuously applying said nutrient medium to said band in liquid condition and wherein after the inoculation of a certain band section with a sample to be examined, a trace of p-nitrophenylglycerin is laid on said band to prevent bacteria from migrating from the section.

* * * * *